United States Patent
Kollar

(10) Patent No.: US 8,522,798 B2
(45) Date of Patent: Sep. 3, 2013

(54) DENTAL FLOSSER WITH IMPROVED STRENGTH

(75) Inventor: Kevin J Kollar, Ada, MI (US)

(73) Assignee: Ranir, LLC, Grand Rapids, MI (US)

( * ) Notice: Subject to any disclaimer, the term of this patent is extended or adjusted under 35 U.S.C. 154(b) by 0 days.

(21) Appl. No.: 13/100,682

(22) Filed: May 4, 2011

(65) Prior Publication Data

US 2012/0279517 A1 Nov. 8, 2012

(51) Int. Cl.
*A61C 15/00* (2006.01)

(52) U.S. Cl.
USPC .................................................. 132/323

(58) Field of Classification Search
USPC .................................................. 132/323
See application file for complete search history.

(56) References Cited

U.S. PATENT DOCUMENTS

| 413,001 | A | * | 10/1889 | Walsh | 132/323 |
| 4,006,750 | A | | 2/1977 | Chodorow | |
| 5,538,023 | A | | 7/1996 | Oczkowski et al. | |
| 5,829,458 | A | * | 11/1998 | Chodorow | 132/323 |
| 7,204,257 | B2 | | 4/2007 | Crossman | |
| 7,487,785 | B2 | | 2/2009 | Dougan et al. | |
| 2005/0039772 | A1 | | 2/2005 | Meindersma | |
| 2008/0104786 | A1 | * | 5/2008 | Hohlbein et al. | 15/167.1 |
| 2008/0149134 | A1 | | 6/2008 | Crossman | |

FOREIGN PATENT DOCUMENTS

| JP | 11318948 | | 11/1999 |
| TW | 483748 | | 4/2002 |
| WO | 8502533 | | 6/1985 |
| WO | WO 85/02533 | * | 6/1985 |

OTHER PUBLICATIONS

Extended European Search Report for Application No. 12165064.2, dated Aug. 20, 2012.

* cited by examiner

*Primary Examiner* — Todd Manahan
*Assistant Examiner* — Brianne Kalach
(74) *Attorney, Agent, or Firm* — Warner Norcross & Judd LLP

(57) ABSTRACT

A dental flosser including a plastic handle having proximal and distal ends, a flosser head at the distal end of the handle, and two spaced apart arms extending from the flosser head. Two distal end portions extend from the arms and secure a strand of floss. The distal end portions may be wider than the respective arms to increase the force required to pull the floss through the distal end portions. The distal end portions may intersect and extend through an interior and exterior plane defined by the interior and exterior surfaces of the arms.

7 Claims, 4 Drawing Sheets

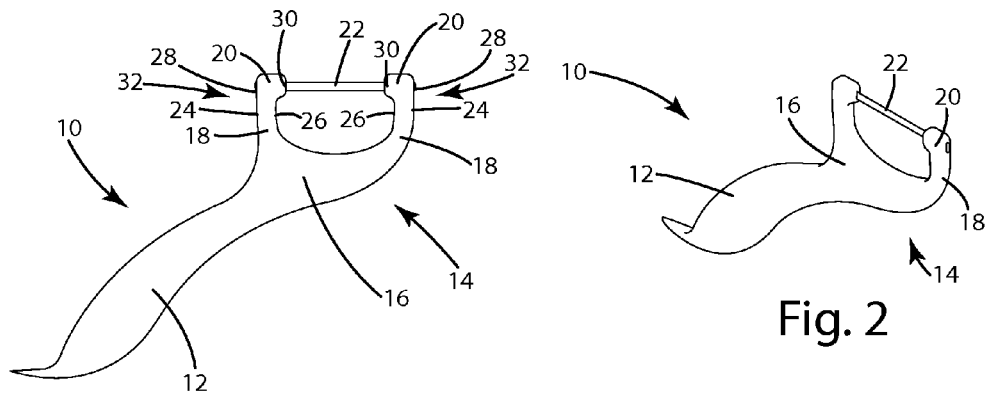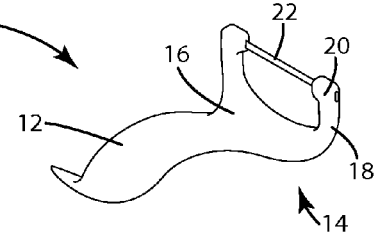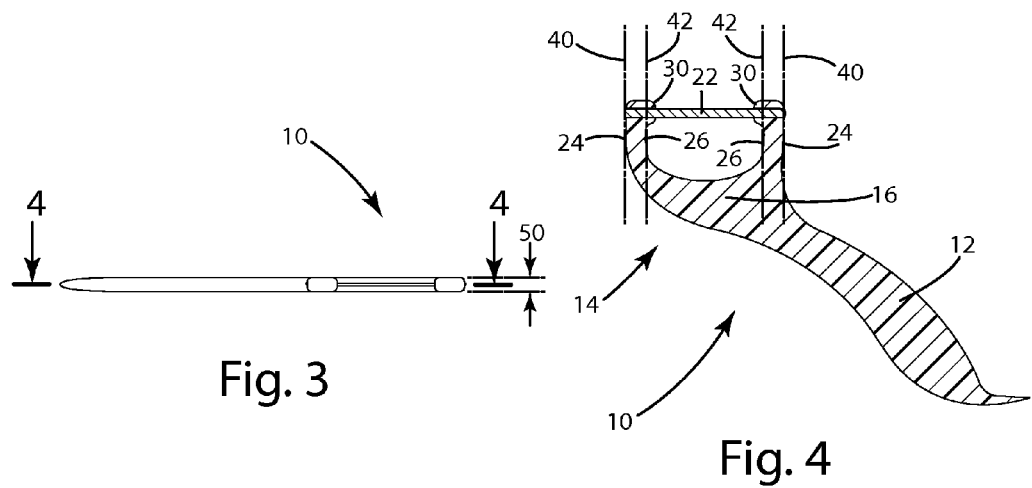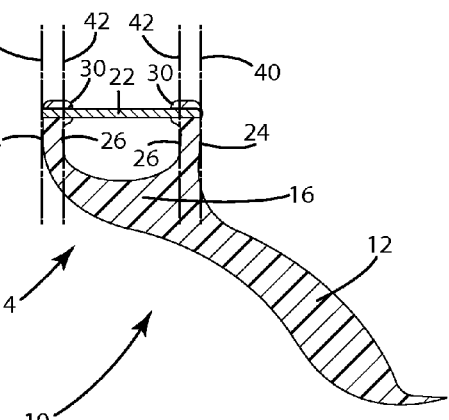

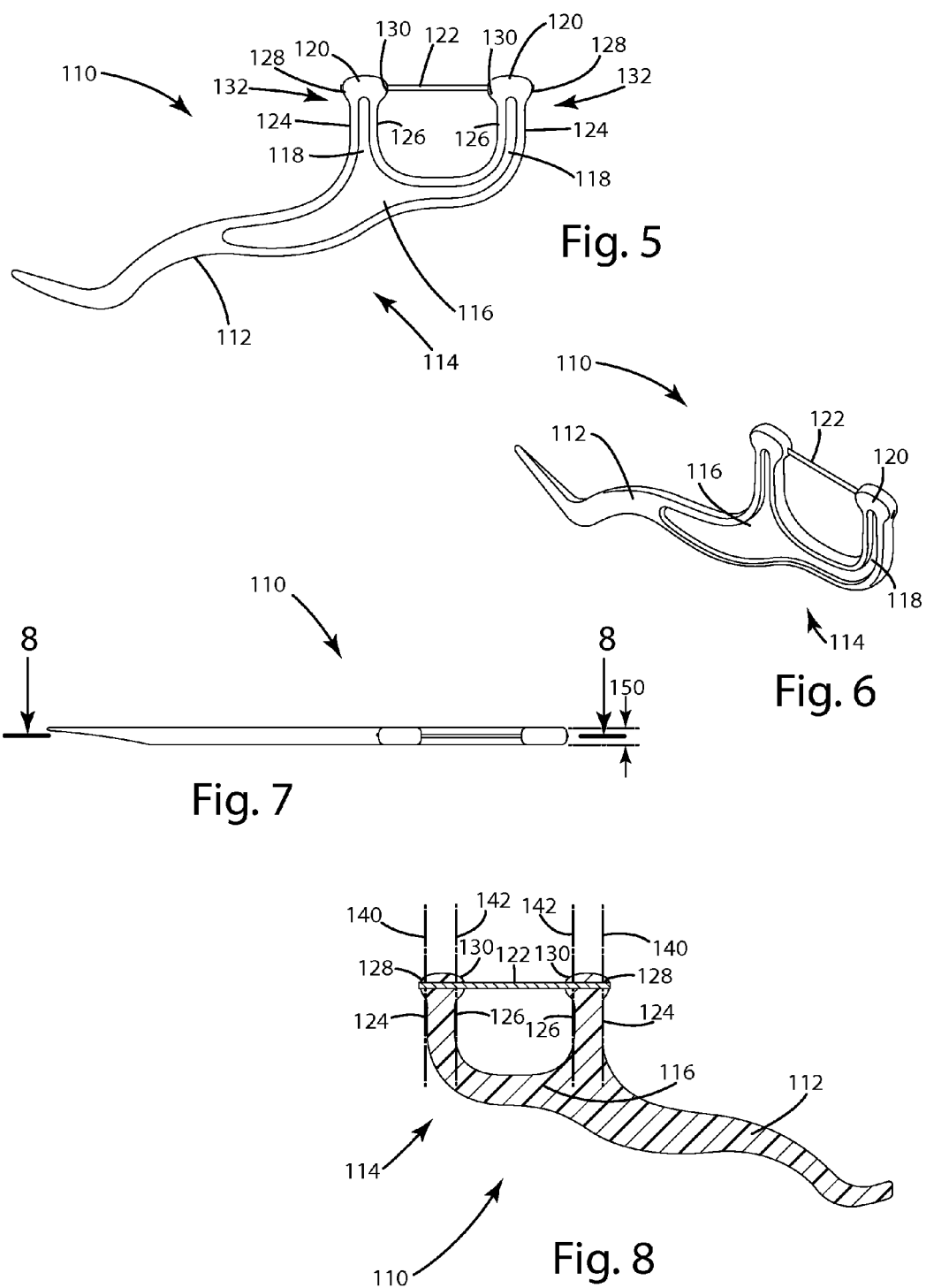

DENTAL FLOSSER WITH IMPROVED STRENGTH

BACKGROUND OF THE INVENTION

The present invention relates to disposable dental floss holders commonly called dental flossers, and more particularly to injection molded dental flossers which each include a handle and a head part with two spaced-apart arms supporting a strand of dental floss.

In more recent years dental flossers have become widely used for removing plaque from tooth surfaces, particularly from the generally facing surfaces of adjacent teeth and for removing food particles from the interstices between adjacent teeth. Such interstices may be empty space or may be merely the interface areas of contact between the surfaces of adjacent teeth. For many persons a dental flosser is substantially easier to use than a conventional strand of dental floss wrapped about fingers of both hands and manipulated between teeth, by having fingers of one hand in the mouth and fingers of the other hand outside the mouth.

Examples of prior art dental flossers are disclosed in U.S. Pat. No. 5,538,023 to Oczkowski et al.; U.S. Pat. Nos. 5,829,458, and 4,006,750 to Chodorow; U.S. Pat. No. 7,204,257 to Crossman; U.S. Pat. No. 7,487,785 to Dougan et al. and U.S. Application No. 2008/0149134 to Crossman.

Typically, prior art dental flossers fail in two ways. First, the floss may pull through one or both arms of the flosser when a sufficiently large force is required to either insert or withdraw the floss between teeth. Second, the floss may break in response to a sufficiently large force. The first failure mode is more common and has been identified as a problem with prior art flossers.

Some designs have attempted to address the failure mode of the floss pulling through the flosser arm. One example is "knotting" the floss after it is molded into the arm of the flosser. Knotting the floss involves (1) trimming the excess floss from the area outside of the flosser arms and (2) applying heat to each trimmed end to create a ball (called a "knot"). The knots on the outside of each flosser arm increase the force required to pull the floss through the arms, but also add steps to the manufacturing process.

SUMMARY OF THE INVENTION

The present invention provides a dental flosser configuration that resists the floss pulling through the distal end portions of the flosser.

In one embodiment, the present invention includes a flosser with a flosser head, a base part and first and second spaced apart arms. The arms each have a proximal portion and a distal end portion. A strand of floss extends between the two distal end portions of the arms. The proximal portions and the distal end portions each have a width parallel to the strand of floss. The width of at least one of the distal end portions is greater than the width of at least one of the proximal portions.

In another embodiment, the widths of the distal end portions are both greater than the widths of the respective proximal portions.

In another embodiment, a first exterior reference plane is defined by the exterior surface of the first proximal portion adjacent the distal end portion and a first interior reference plane is defined by the interior surface of the first proximal portion adjacent the distal end portion. The first exterior and first interior reference planes are substantially perpendicular to the strand of floss. The first distal end portion spans the distance between the first interior reference plane and the first exterior reference plane and extends beyond at least one of the first exterior reference plane and the first interior reference plane.

In another embodiment, a second exterior reference plane is defined by the exterior surface of the second proximal portion adjacent the distal end portion and a second interior reference plane is defined by the interior surface of the second proximal portion adjacent the distal end portion. The second exterior and second interior reference planes are substantially perpendicular to the strand of floss. The second distal end portion spans the distance between the second interior reference plane and the second exterior reference plane and extends beyond at least one of the second exterior reference plane and the second interior reference plane.

In another embodiment, both the first distal end portion and the second distal end portion extend through the respective exterior and interior reference planes.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and may be practiced or carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 1 is a front view of a dental flosser according to one embodiment of the present invention;

FIG. 2 is a perspective view of the flosser of FIG. 1;

FIG. 3 is a top view of the flosser of FIG. 1;

FIG. 4 is a sectional view of the flosser of FIG. 1 taken along line 4-4 in FIG. 3;

FIG. 5 is a front view of a dental flosser according to a second embodiment of the present invention;

FIG. 6 is a perspective view of the flosser of FIG. 5;

FIG. 7 is a top view of the flosser of FIG. 5;

FIG. 8 is a sectional view of the flosser of FIG. 5 taken along line 8-8 in FIG. 7;

DETAILED DESCRIPTION OF THE CURRENT EMBODIMENTS

Figure 9:
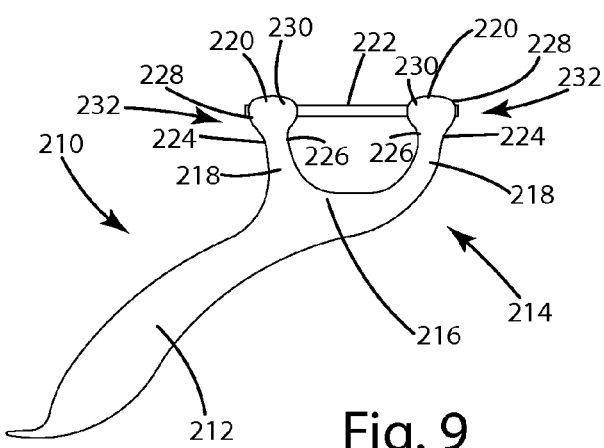
FIG. 9 is a front view of a dental flosser according to a third embodiment of the present invention.
Figure 10:
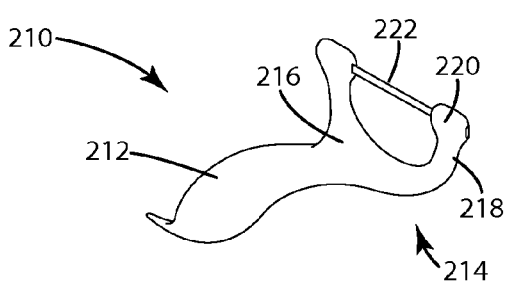
FIG. 10 is a perspective view of the flosser of FIG. 9.
Figure 11:
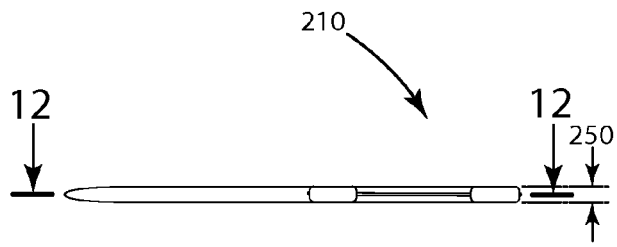
FIG. 11 is a top view of the flosser of FIG. 9.

A dental flosser according to one embodiment of the present invention is shown in FIGS. 1-4 and generally designated 10. In one embodiment, the flosser 10 includes a plastic handle part 12 and flosser head 14. The handle part 12 includes a first proximal end and a second distal end. The flosser head 14 has a generally U-shape or V-shape comprising a base part 16 and a pair of spaced apart arms 32 extending from the base part 16 which may be generally parallel to each other. Each of the arms 32 has a proximal portion 18 extending from the base and a distal end portion 20 extending from the proximal portion 18. Each of the proximal portions 18 have an exterior surface 24 and an interior surface 26. Each of the distal end portions 20 have an exterior end portion 28 and an interior end portion 30. The interior end portions 30 may converge such that the interior end portions 30 are closer together than the interior surfaces 26 of the proximal portions 18. The handle 12, head 14, base part 16 and arms 32 may be made of any of a variety of materials, including polystyrene and polypropylene.

Extending transversely between and fixed to the distal end portions 20 of each flosser is a strand of dental floss 22. The strand may be made of any of a variety of materials, including nylon, Teflon®, PTFE, and UHMWPE. If UHMWPE is used, it may be a 400 denier UHMWPE strand that includes 120 microfilaments configured with a Z twist, as are available from Honeywell International Inc. or other commercial suppliers. The nylon, PTFE or Teflon® floss is also readily available from many commercial sources. If PTFE is used, it may be a 200 denier strand. In other embodiments, the floss 22 may be provided with a coating, such as a wax coating or another coating that changes the coefficient of friction. Other types of coatings include flavor agents, oral care agents and abrasives.

As shown in FIG. 4, exterior reference planes 40 are defined by the exterior surfaces 24 and interior reference planes 42 are defined by the interior surfaces 26. The reference planes 40, 42 are substantially perpendicular to the strand of floss 22 and are positioned at the transition between the proximal portions 18 and the distal end portions 20 of the arms 32. In some embodiments, this may be the location where the width of the arms 32 begins to increase. In the embodiment shown in FIG. 4, the interior end portions 30 intersect and extend through the interior reference planes 42. This increase in width provides a greater surface area interaction between the distal end portions 20 and the strand of dental floss 22, which results in a greater force required to pull the dental floss 22 through the distal end portions 20. One or both of the distal end portions 20 may have a width greater than the width of the proximal portions 18, when taken perpendicular to the floss 22. In this manner, one or both of the distal end portions 20 may span the distance between the respective exterior and interior reference planes 40, 42 and may extend beyond one or both of the respective reference planes 40, 42.

The flosser 10 may be dimensioned to decrease bulkiness and material usage, while at the same time providing sufficient strength. The proximal portions 18 may be a variety of lengths (between the base 16 and the distal end portions 20), including between approximately 0.34 and 0.44 inches, and further including approximately 0.39 inches. As used herein, the term "length" generally indicates a direction substantially perpendicular to the floss 22. The proximal portions 18 may also be a variety of widths (between exterior surface 24 and interior surface 26), including between approximately 0.08 and 0.18 inches, and further including approximately 0.13 inches. As used herein, the term "width" generally indicates a direction substantially perpendicular to the floss 22. The distal end portions 20 may be a variety of lengths, including between approximately 0.09 and 0.19 inches, and further including approximately 0.14 inches. The distal end portions 20 may also be a variety of widths, including between approximately 0.14 and approximately 0.24 inches and further including approximately 0.19 inches. The length and width of each proximal portion 18 may also have a predetermined relationship with the length and width of the respective distal end portion 20. For example, the width of the distal end portions 20 may be between approximately 30% and 60% greater than the width of the respective proximal portions 18 and may optionally be approximately 45% greater than the width of the respective proximal portions 18. Also by way of example, the length of the proximal portions 18 may be between approximately 160% and 190% greater than the length of the respective distal end portions 20 and may optionally be approximately 175% greater than the length of the respective distal end portions 20. It is also contemplated that only one of the distal end portions 20 may be enlarged as described above. The flosser 10 also has a thickness 50, which may be any of a variety of values, including between approximately 0.04 and 0.14 inches, and further including approximately 0.09 inches.

Manufacture of the flosser 10 may be conducted in a conventional manner, for instance, by injection molding the flosser 10 in a mold, with the strand of floss placed in the mold prior to molding, such that the arms 32 and distal end portions 20 of the flosser 10 are molded about the strand of dental floss. In one embodiment, multiple flossers 10 may be formed simultaneously in a multi-cavity mold where the plurality of cavities are aligned so that each of the strands can be extended in a straight line transversely across all the distal end portions 20 of the aligned flosser cavities. The strand of floss is positioned in grooves in a mold surface between the cavities, so that on closing the mold parts the strand is not crushed. The strand is placed in tension (a) to make sure it remains straight while traversing the distal end portions 20 of the flosser cavities and remains in the grooves between the cavities, and (b) to incorporate a pre-stretch in the strand to reduce the stretching that might occur in use. For example, a PTFE strand may be stretched about 15% and a UHMWPE strand may be stretched about 3½%. Additionally, the strand of floss may be twisted. For example, a UHMWPE strand may be given about four twists per inch by known twisting techniques to enhance the strength and resistance to stretching of the UHMWPE floss strand to about 3% as compared to a stretch of about 3½% without the further twists.

A variety of different injection molded plastics may be used to form the handle part 12 and the head part 14. Examples include polystyrene or polypropylene. Both of these plastics have melting temperatures below that of PTFE and/or UHMWPE, so that the dental floss will not be melted or otherwise damaged when the molten plastic for the distal end portions of the flosser is injected around and about the outer surfaces of the portions of the floss extending across the distal end portions of the flosser in the mold cavity.

Conventional multi-cavity injection mold and manufacturing techniques produce skeleton-connected aligned molded flossers, with a continuous strand of floss extending transversely through the distal end portions 20 of the aligned flossers. These flossers may subsequently be separated by severing the segments of floss extending between the distal end portions 20 of adjacent flossers. Because of the greater surface area interaction between the distal end portions 20 and the strand of dental floss 22 described above, it may not be necessary to knot the floss at the outside of the distal end portions 20 to prevent the floss from pulling through during use of the flosser. However, if increased strength is desired, the severing of the floss may be made by a hot knife, laser or flame. By this technique the exposed ends of the strands are melted and formed into beads having greater diameter or greater cross-sectional area than that of the original strands, thus restricting the portion of each strand embedded in the distal end portion from pull through. The bead may be a single mass of the melted fibers of the strands or multiple tiny beads of the coalesced ends of the fibers and appearing somewhat like a cauliflower. If necessary, the strands may be retained in the distal end portions 20 or by chemically bonding the floss material to the material used to form the distal end portions 20.

A second embodiment of the dental flosser is shown in FIGS. 5-8. In this embodiment, the dental flosser 110 includes a handle part 112 and a head part 114 that are substantially similar to the dental flosser 10 described above. The head part 114 includes a base 116 and a pair of arms 132 extending from the base 116. In this embodiment, the exterior end portions 128 diverge such that the exterior end portions 128 are farther apart than the exterior surfaces 124 of proximal portions 118. In this embodiment, the interior end portions 130 converge such that the interior end portions 130 are closer together than the interior surfaces 126 of the proximal portions 118. As shown in FIG. 8, exterior reference planes 140 are defined by the exterior surfaces 124 and interior reference planes 142 are defined by the interior surfaces 126 in the same manner described in connection with the first embodiment. In the embodiment shown in FIG. 8, the exterior end portions 128 intersect and extend through the exterior reference planes 140 and the interior end portions 130 intersect and extend through the interior reference planes 142. This increase in width provides a greater surface area interaction between the distal end portions 120 and the strand of dental floss 122, which results in a greater force required to pull the dental floss 122 through the distal end portions 120. One or both of the distal end portions 120 may have a width greater than the width of the proximal portions 118, when taken perpendicular to the floss 122. In this manner, one or both of the distal end portions 120 may span the distance between the respective exterior and interior reference planes 140, 142 and may extend beyond one or both of the respective reference planes 140, 142.

As mentioned above in connection with the first embodiment, the flosser 110 may be dimensioned to decrease bulkiness and material usage, while at the same time providing sufficient strength. The proximal portions 118 may be a variety of lengths (between the base 116 and the distal end portions 120), including between approximately 0.38 and 0.48, and further including approximately 0.43 inches. The proximal portions 118 may also be a variety of widths (between exterior surface 124 and interior surface 126), including between approximately 0.1 and 0.2 inches, and further including approximately 0.15 inches. The distal end portions 120 may be a variety of lengths, including between approximately 0.08 and 0.18 inches, and further including approximately 0.13 inches. The distal end portions 120 may also be a variety of widths, including between approximately 0.18 and approximately 0.28 inches and further including approximately 0.23 inches. The length and width of each proximal portion 118 may also have a predetermined relationship with the length and width of the respective distal end portion 120. For example, the width of the distal end portions 120 may be between approximately 40% and 70% greater than the width of the respective proximal portions 118 and may optionally be approximately 55% greater than the width of the respective proximal portions 118. Also by way of example, the length of the proximal portions 118 may be between approximately 215% and 245% greater than the length of the respective distal end portions 120 and may optionally be approximately 230% greater than the length of the respective distal end portions 120. It is also contemplated that only one of the distal end portions 120 may be enlarged as described above. The flosser 110 also has a thickness 150, which may be any of a variety of values, including between approximately 0.04 and 0.14 inches, and further including approximately 0.09 inches.

Figure 12:
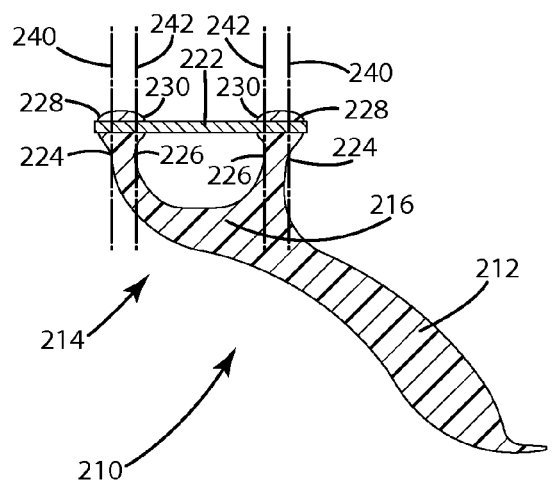
FIG. 12 is a sectional view of the flosser of FIG. 9 taken along line 12-12 in FIG. 11.
Figure 13:
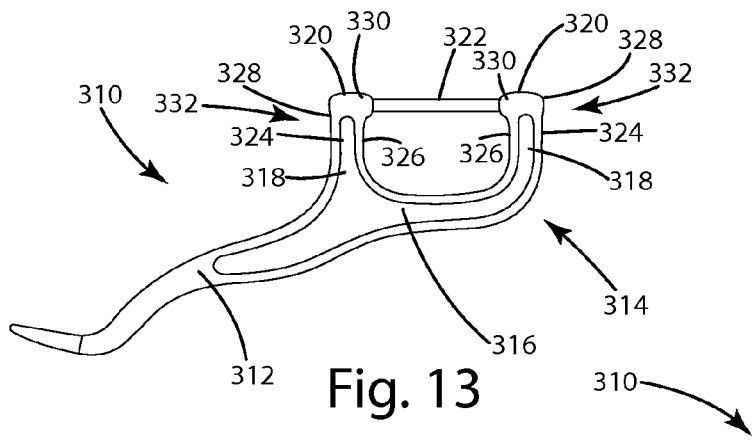
FIG. 13 is a front view of a dental flosser according to a fourth embodiment of the present invention.
Figure 14:
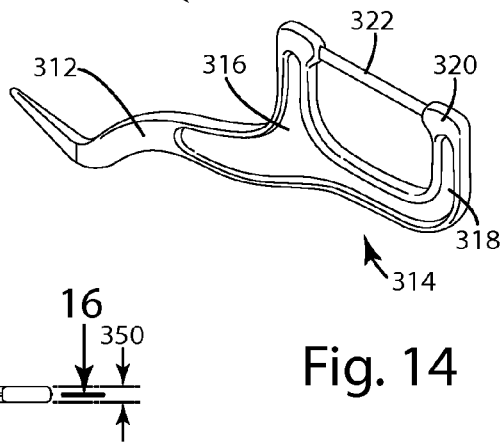
FIG. 14 is a perspective view of the flosser of FIG. 13.
Figure 15:
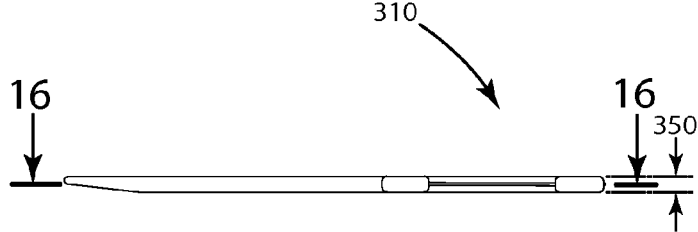
FIG. 15 is a top view of the flosser of FIG. 13.

A third embodiment of the dental flosser is shown in FIGS. 9-12 and includes a "Y-shaped" configuration. In this embodiment, the dental flosser 210 includes a handle part 212 and a head part 214 that are substantially similar to the dental flosser 10 described above. The head part 214 includes a base 216 and a pair of arms 232 extending from the base 216. In this embodiment, the exterior end portions 228 diverge such that they are farther apart than the exterior surfaces 224 of proximal portions 218 and the interior end portions 230 converge such that they are closer together than the interior surfaces 226 of proximal portions 218. As shown in FIG. 12, exterior reference planes 240 are defined by the exterior surfaces 224 and interior reference planes 242 are defined by the interior surfaces 226 in the same manner described in connection with the first embodiment. In the embodiment shown in FIG. 12, the exterior end portions 228 intersect and extend through the exterior reference planes 240 and the interior end portions 230 intersect and extend through the interior reference planes 242. This increase in width provides a greater surface area interaction between the distal end portions 220 and the strand of dental floss 222, which results in a greater force required to pull the dental floss 222 through the distal end portions 220. One or both of the distal end portions 220 may have a width greater than the width of the proximal portions 218, when taken perpendicular to the floss 222. In this manner, one or both of the distal end portions 220 may span the distance between the respective exterior and interior reference planes 240, 242 and may extend beyond one or both of the respective reference planes 240, 242.

As mentioned above in connection with the other embodiments, the flosser 210 may be dimensioned to decrease bulkiness and material usage, while at the same time providing sufficient strength. The proximal portions 218 may be a variety of lengths (between the base 216 and the distal end portions 220), including between approximately 0.37 and 0.47 inches, and further including approximately 0.42 inches. The proximal portions 218 may also be a variety of widths (between exterior surface 224 and interior surface 226), including between approximately 0.09 and 0.19 inches, and further including approximately 0.14 inches. The distal end portions 220 may be a variety of lengths, including between approximately 0.13 and 0.23 inches, and further including approximately 0.18 inches. The distal end portions 220 may also be a variety of widths, including between approximately 0.23 and approximately 0.33 inches and further including approximately 0.28 inches. The length and width of each proximal portion 218 may also have a predetermined relationship with the length and width of the respective distal end portion 220. For example, the width of the distal end portions 220 may be between approximately 85% and 115% greater than the width of the respective proximal portions 218 and may optionally be approximately 100% greater than the width of the respective proximal portions 218. Also by way of example, the length of the proximal portions 218 may be between approximately 120% and 150% greater than the length of the respective distal end portions 220 and may optionally be approximately 135% greater than the length of the respective distal end portions 220. It is also contemplated that only one of the distal end portions 220 may be enlarged as described above. The flosser 210 also has a thickness 250, which may be any of a variety of values, including between approximately 0.03 and 0.13 inches, and further including approximately 0.08 inches.

Figure 16:
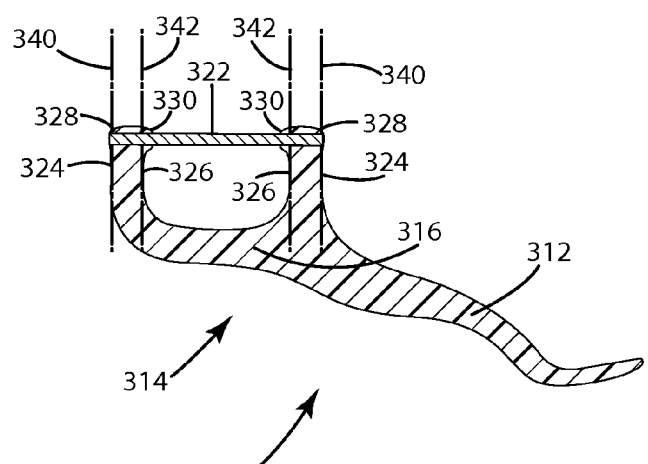
FIG. 16 is a sectional view of the flosser of FIG. 13 taken along line 16-16 in FIG. 13.

A fourth embodiment of the dental flosser is shown in FIGS. 13-16. In this embodiment, the dental flosser 310 includes a handle part 312 and a head part 314 that are substantially similar to the dental flosser 10 described above. The head part 314 includes a base 316 and a pair of arms 332 extending from the base 316. In this embodiment, the interior end portions 330 converge such that the interior end portions 330 are closer together than the interior surfaces 326 of the proximal portions 318. As shown in FIG. 16, exterior reference planes 340 are defined by the exterior surfaces 324 and interior reference planes 342 are defined by the interior surfaces 326 in the same manner described in connection with the first embodiment. In the embodiment shown in FIG. 16, the interior end portions 330 intersect and extend through the interior reference planes 342. This increase in width provides a greater surface area interaction between the distal end portions 320 and the strand of dental floss 322, which results in a greater force required to pull the dental floss 322 through the distal end portions 320. One or both of the distal end portions 320 may have a width greater than the proximal portions 318, when taken perpendicular to the floss 322. In this manner, one or both of the distal end portions 320 may span the distance between the respective exterior and interior reference planes 340, 342 and may extend beyond one or both of the respective reference planes 340, 342.

As mentioned above in connection with the other embodiments, the flosser 310 may be dimensioned to decrease bulkiness and material usage, while at the same time providing sufficient strength. The proximal portions 318 may be a variety of lengths (between the base 316 and the distal end portions 320), including between approximately 0.38 and 0.48 inches, and further including approximately 0.43 inches. The proximal portions 318 may also be a variety of widths (between exterior surface 324 and interior surface 326), including between approximately 0.13 and 0.23 inches, and further including approximately 0.18 inches. The distal end portions 320 may be a variety of lengths, including between approximately 0.08 and 0.18 inches, and further including approximately 0.13 inches. The distal end portions 320 may also be a variety of widths, including between approximately 0.18 and approximately 0.28 inches and further including approximately 0.23 inches. The length and width of each proximal portion 318 may also have a predetermined relationship with the length and width of the respective distal end portion 320. For example, the width of the distal end portions 320 may be between approximately 15% and 45% greater than the width of the respective proximal portions 318 and may optionally be approximately 30% greater than the width of the respective proximal portions 318. Also by way of example, the length of the proximal portions 318 may be between approximately 215% and 245% greater than the length of the respective distal end portions 320 and may optionally be approximately 230% greater than the length of the respective distal end portions 320. It is also contemplated that only one of the distal end portions 320 may be enlarged as described above. The flosser 310 also has a thickness 350, which may be any of a variety of values, including between approximately 0.04 and 0.14, and further including approximately 0.09.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Additionally, any of the features from one embodiment may be used in another embodiment. Any reference to claim elements in the singular, for example, using the articles "a," "an," "the" or "said," is not to be construed as limiting the element to the singular.

The invention claimed is:

1. A dental flosser comprising:
a plastic handle having two ends;
a flosser head at one of the ends of the handle;
the flosser head including a base part, two spaced apart arms, and a strand of floss molded to the arms, the first arm having a first proximal portion extending from the base and a first distal end portion extending from the first proximal portion, the second arm having a second proximal portion extending from the base and second distal end portion extending from the second proximal portion, the first and second arms and the first and second distal end portions each defining a width generally parallel to the strand of floss, wherein the distal end portions have a greater width than their respective proximal portions, the wider distal end portions increasing the force required to detach the floss from the arms, wherein the lengths and widths of the proximal portions have a predetermined relationship with respect to the lengths and widths of the respective distal end portions in order to decrease bulkiness and material usage while maintaining strength, wherein the first and second distal end portions each define a first length and a first width, and the first and second proximal portions each define a second length and a second width, wherein the first length is between 0.13 inches and 0.23 inches and the first width is between 0.23 inches and 0.33 inches, and wherein the second length is between 0.37 inches and 0.47 inches and the second width is between 0.09 inches and 0.19 inches.

2. The dental flosser according to claim 1 including:
each of the first and second proximal portions having an exterior surface and an interior surface;
a first exterior reference plane defined by the exterior surface of the first proximal portion adjacent the first distal end portion, the first exterior reference plane substantially perpendicular to the strand of floss;
a first interior reference plane defined by the interior surface of the first proximal portion adjacent the first distal end portion, the first interior reference plane substantially perpendicular to the strand of floss; and a second exterior reference plane defined by the exterior surface of the second proximal portion adjacent the second distal end portion, the second exterior reference plane substantially perpendicular to the strand of floss; and a second interior reference plane defined by the interior surface of the second proximal portion adjacent the second distal end portion, the second interior reference plane substantially perpendicular to the strand of floss, wherein the second distal end portion spans the distance between the second exterior reference plane and the second interior reference plane and extends beyond at least one of the second exterior reference plane and the second interior reference plane.

3. The dental flosser according to claim 2 wherein the first distal end portion has a width parallel to the strand of floss, wherein the width of the first distal end portion is between approximately 0.14 and 0.28 inches.

4. The dental flosser according to claim 2 wherein the plastic handle is molded from a styrene.

5. The dental flosser according to claim 4 wherein the first distal end portion extends beyond the first exterior reference plane and the first interior reference plane and wherein the second distal end portion extends beyond the second exterior reference plane and the second interior reference plane.

6. The dental flosser according to claim 5 wherein the first and second distal end portions each have a width parallel to the strand of floss, wherein the width of the first distal end portion and the width of the second distal end portion are each between approximately 0.18 and 0.28 inches.

7. A dental flosser comprising:

a plastic handle having two ends;

a flosser head at one of the ends of the handle;

the flosser head including a base part, two spaced apart arms, and a strand of floss molded to the arms, the first arm having a first proximal portion extending from the base and a first distal end portion extending from the first proximal portion, the second arm having a second proximal portion extending from the base and second distal end portion extending from the second proximal portion, the first and second arms and the first and second distal end portions each defining a width generally parallel to the strand of floss, wherein the distal end portions have a greater width than their respective proximal portions, the wider distal end portions increasing the force required to detach the floss from the arms, wherein the lengths and widths of the proximal portions have a predetermined relationship with respect to the lengths and widths of the respective distal end portions in order to decrease bulkiness and material usage while maintaining strength, wherein the first and second distal end portions each define a first length and a first width, and the first and second proximal portions each define a second length and a second width, wherein the second first length is between 0.09 inches and 0.19 inches and the first width is between 0.14 inches and 0.24 inches, and wherein the second length is between 0.34 inches and 0.44 inches and the second width is between 0.08 inches and 0.18 inches.

* * * * *